United States Patent
Force et al.

(10) Patent No.: US 9,650,453 B2
(45) Date of Patent: May 16, 2017

(54) METHODS OF INTEGRATING ALUMINOXANE PRODUCTION INTO CATALYST PRODUCTION

(71) Applicant: Univation Technologies, LLC, Houston, TX (US)

(72) Inventors: Randall L. Force, Charleston, WV (US); Timothy R. Lynn, Glen Gardner, NJ (US); Michael D. Awe, Langhorne, PA (US)

(73) Assignee: Univation Technologies, LLC, Houston, TX (US)

( * ) Notice: Subject to any disclaimer, the term of this patent is extended or adjusted under 35 U.S.C. 154(b) by 8 days.

(21) Appl. No.: 14/653,449

(22) PCT Filed: Dec. 19, 2013

(86) PCT No.: PCT/US2013/076461
§ 371 (c)(1),
(2) Date: Jun. 18, 2015

(87) PCT Pub. No.: WO2014/105614
PCT Pub. Date: Jul. 3, 2014

(65) Prior Publication Data
US 2015/0315308 A1 Nov. 5, 2015

Related U.S. Application Data

(60) Provisional application No. 61/746,761, filed on Dec. 28, 2012.

(51) Int. Cl.
*C08F 110/00* (2006.01)
*C07F 5/06* (2006.01)
*B01J 31/14* (2006.01)
*C08F 10/00* (2006.01)

(52) U.S. Cl.
CPC ............ *C08F 110/00* (2013.01); *C07F 5/068* (2013.01); *B01J 31/14* (2013.01); *C08F 10/00* (2013.01)

(58) Field of Classification Search
CPC ........... C07F 5/068; B01J 31/14; B01J 31/143
USPC ......... 502/111, 113, 117, 355; 423/111, 625, 423/628, 630
See application file for complete search history.

(56) References Cited

U.S. PATENT DOCUMENTS

| | | | | |
|---|---|---|---|---|
| 5,157,008 A * | 10/1992 | Sangokoya | ............. | C07F 5/068 502/111 |
| 5,446,001 A * | 8/1995 | Gurtzgen | ............... | B01J 19/246 502/104 |
| 5,599,964 A | 2/1997 | Roberg et al. | | |
| 5,606,087 A * | 2/1997 | Roberg | .................... | C07F 5/068 423/625 |
| 6,124,229 A * | 9/2000 | Becker | .................... | B01J 31/143 502/102 |
| 2002/0086957 A1 * | 7/2002 | Wu | ........................ | B01J 31/143 526/110 |
| 2012/0071679 A1 | 3/2012 | Fang et al. | | |

FOREIGN PATENT DOCUMENTS

GB 1176692 1/1970
WO 2010/144130 * 12/2010 .............. C07F 17/00

* cited by examiner

*Primary Examiner* — Patricia L Hailey
(74) *Attorney, Agent, or Firm* — Brooks, Cameron & Huebsch, PLLC

(57) ABSTRACT

Methods for integrating aluminoxane production into catalyst production are disclosed.

19 Claims, 2 Drawing Sheets ced solvent and a first quantity of a hydrocarbyl alu-
METHODS OF INTEGRATING ALUMINOXANE PRODUCTION INTO CATALYST PRODUCTION This application is a National Stage Application under 35 U.S.C. §371 of International Application Number PCT/US2013/076461, filed Dec. 19, 2013 and published as WO 2014/105614 on Jul. 3, 2014, which claims the benefit to U.S. Provisional Application 61/746,761, filed Dec. 28, 2012, the entire contents of which are incorporated herein by reference in its entirety.

BACKGROUND

Advances in polymerization and catalysts have produced new polymer resins having improved physical and mechanical properties useful in a wide variety of products and applications. With the development of new catalysts, the choice of polymerization, such as solution, slurry, high pressure or gas phase, for producing a particular polymer has been greatly expanded. Advances in polymerization technology have also provided more efficient, highly productive, and economically enhanced processes.

Polymerization catalysts may be combined with an activator to yield improved catalyst compositions. Methylaluminoxane ("MAO") is a common activator for catalysts that produce polyethylene and other polyolefins. While MAO can provide improved catalyst functionality, the MAO is typically a major component of catalyst cost. Approximately half of the total cost of the MAO can be attributed to its trimethylaluminum ("TMA") precursor. Additionally, as MAO is pyrophoric and reactive with any chemical bearing an acidic proton, it may require special storage, handling, and transport measures. Thus, cost savings could be achieved by processes that more efficiently use the TMA precursor or minimize the amount of storage, handling, and transport needed for the MAO.

A common process for producing MAO utilizes a controlled hydrolysis of a dilute TMA solution to form MAO and methane. The hydrolysis reaction is typically carried out in a solvent, such as toluene, which can increase the efficiency of the hydrolysis reaction. While helping to absorb the heat of the TMA hydrolysis, the excess toluene may also be needed to keep the MAO in solution and ensure that water concentrations remain low. The MAO production process may also include refining by means of a flash evaporation to recover some of the toluene and unreacted TMA while concentrating the MAO from less than 10 weight percent up to approximately 30 weight percent in toluene for shipment. Although shipping the MAO in this concentrated MAO solution is common, there are drawbacks to this MAO production process. For example, the concentrated MAO solution still contains unreacted TMA that may not be consumed in the subsequent catalyst manufacturing operation, which must ultimately be disposed. In addition, significant quantities of toluene from the concentrated MAO solution are also passed through the catalyst production process as a waste stream. The concentrated MAO solution may also have a limited shelf life before coagulating into an unusable gel, even when kept in cold storage. In some instances, stabilizers may be added at an additional expense to create a modified MAO with improved shelf life.

SUMMARY

Disclosed herein are methods for integrating aluminoxane production into catalyst production that comprises reacting a hydrocarbyl aluminum compound and an oxygen source in a recycled solvent to produce at least a reaction mixture comprising an aluminoxane, a remainder of the hydrocarbyl aluminum compound, and the recycled solvent; combining at least a portion of the reaction mixture with a catalyst component to produce at least the catalyst composition; separating the catalyst composition from the recycled solvent in the portion of the reaction mixture; and recycling at least a portion of the separated solvent for producing additional aluminoxane, the separated solvent comprising at least a portion of the remainder of the hydrocarbyl aluminum compound. The oxygen source may be water or another suitable oxygen source.

Further disclosed herein are methods for integrating aluminoxane production into catalyst production that comprises circulating a fluid in a reactor loop, the fluid comprising a recycled solvent and a first quantity of a hydrocarbyl aluminum compound; introducing an oxygen source and a second quantity of a hydrocarbyl aluminum compound into the reactor loop; allowing the oxygen source and the hydrocarbyl aluminum compound to react in the solvent to produce at least a reaction mixture comprising an aluminoxane, a remainder of the hydrocarbyl aluminum compound, and the recycled solvent; introducing a catalyst component into the reactor loop to produce at least the catalyst composition; separating the catalyst composition from the recycled solvent; and recycling at least a portion of the separated solvent for producing additional aluminoxane, the separated solvent comprising at least a portion of the remainder of the hydrocarbyl aluminum compound. The oxygen source may be water or another suitable oxygen source.

BRIEF DESCRIPTION OF THE DRAWINGS

These drawings illustrate certain aspects of embodiments of the disclosed methods and should not be used to limit or define the invention.

DETAILED DESCRIPTION

Figure 1:
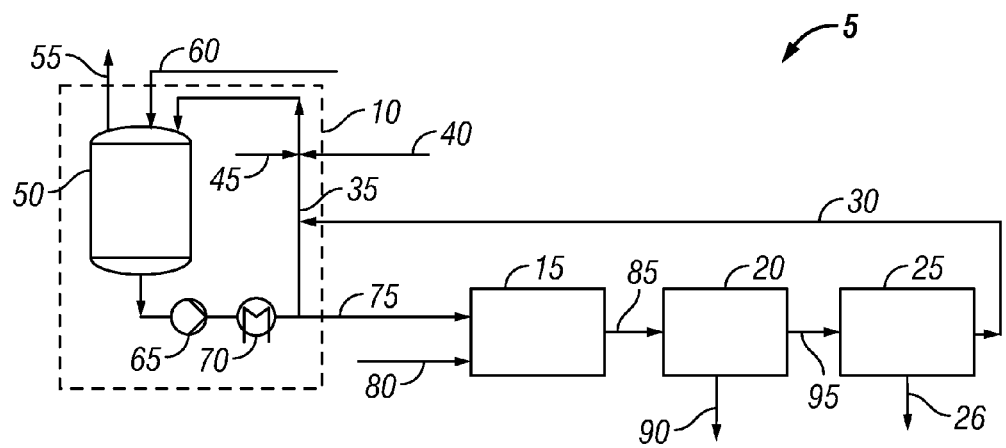
FIG. 1 is a schematic diagram illustrating an example method for catalyst production that includes integrated aluminoxane production.

This disclosure is generally directed to methods for integrating aluminoxane production into catalyst production. In particular embodiments, aluminoxane production may be integrated into catalyst production, in which a stream comprising a solvent and unreacted hydrocarbyl aluminum compound(s) ("HAC") may be recovered in the catalyst production and recycled as a feed to aluminoxane production.

There may be several potential advantages to the methods and systems disclosed herein, only some of which may be discussed in the present disclosure. One of the many potential advantages of the methods and systems is that costs conventionally associated with aluminoxanes may be reduced. For example, large volumes of solvent in which the aluminoxanes are typically shipped have conventionally been collected during catalyst production, requiring disposal of a large volume of material. However, with integration of aluminoxane production, at least a portion of this collected solvent can be recycled as a feed for production of additional aluminoxane instead of using fresh solvent. In addition, unreacted HAC contained in the collected solvent can also be recycled for production of additional aluminoxane, reducing the HAC requirements. By way of further example, wastes associated with spoilage of aluminoxanes due to their limited shelf life can also be reduced as integration of aluminoxane production into the catalyst production systems allows for production of aluminoxane on a just in time basis, thus reducing the need to store significant quantities of aluminoxanes. Additionally, costs associated with storing concentrated solutions of aluminoxane may be reduced or even eliminated if aluminoxane production is integrated into catalyst production.

Catalyst Production Methods

Described herein are methods for catalyst production that include integrated aluminoxane production. An aluminoxane may be produced by a hydrolysis reaction of an HAC and water. This hydrolysis reaction, or other reactions to produce aluminoxane, may occur in the presence of a solvent. Aluminoxane carried in the solvent may then be combined with other catalyst components to form a catalyst composition, which may be a supported catalyst composition, for example. The aluminoxane produced in the hydrolysis reaction, or another reaction, may not need to be concentrated prior to combination with the other catalyst components. The catalyst composition may then be separated from the solvent, and the solvent may be recycled as a feed for further use in the preparation of additional aluminoxanes. The solvent may also carry a quantity of unreacted HAC from the hydrolysis reaction such that the unreacted HAC may be recycled with the solvent.

In general, aluminoxanes are compounds that may be used to enhance the ability of a catalyst to oligomerize or polymerize unsaturated monomers, such as olefins. It should be understood that the catalysts may be activated for oligomerization and/or polymerization catalysis in any manner sufficient to allow coordination or cationic oligomerization and/or polymerization. For example, aluminoxanes may activate catalyst compounds to yield compounds having a vacant coordination site that will, for example, coordinate, insert, and polymerize unsaturated monomers, such as olefins. Aluminoxanes may include linear, cyclic, caged, or polymeric structures. Aluminoxanes that may be particularly suitable for use in olefin polymerization catalysts include, for example, oligomeric compounds containing —Al(R)—O subunits, wherein R is an alkyl group. In some embodiments, R may be a $C_1$ to $C_8$ alkyl group. The aluminoxanes may contain linear, cyclic, caged, and/or cross-linked species. Examples of aluminoxanes include methylaluminoxane ("MAO"), modified methylaluminoxane ("MMAO"), ethylalumoxane, and isobutylalumoxane. MMAO's generally may be more soluble in aliphatic solvents and more stable in storage. To improve the solubility of MAO's, higher alkyl groups (e.g., $C_2$ to $C_{20}$ alkyl groups) can be included. MMAO's may contain, for example, up to about 20 mole percent, based on aluminum, of moieties derived from amines, alcohols, esters, phosphoric, and carboxylic acids, thiols, alkyl and aryl disiloxanes to improve activity, solubility, and/or stability.

Aluminoxanes may be produced by the hydrolysis of HACs. Any HAC or mixture of HACs may be used that are capable of reacting with water to produce an aluminoxane. Examples of HACs include alkylaluminum, triarylaluminum, mixed alkyl arylaluminum, alkylaluminum hydride, and the like. The HACs may include alkylaluminum compounds, such as trialkylaluminum compounds, which may include trimethylaluminum, triethylaluminum, triisobutylaluminum, tri-n-hexylaluminum, trioctylaluminum, and the like. The trialkylaluminum compounds include $C_1$ to $C_4$ alkylaluminum compounds. An example technique for producing aluminoxanes via a hydrolysis reaction is described in U.S. Pat. No. 5,606,087.

The hydrolysis reaction of the HACs and water may occur in the presence of a solvent. The solvent may have a boiling point above about 60° C. Examples of suitable solvents include aliphatic and aromatic hydrocarbons, such as toluene, xylene, benzene, and/or hexane.

The water may be added to the reaction either neat or dispersed in the solvent, for example. The proportion of reactants for the hydrolysis reaction may be from about 0.5 moles to about 8.0 moles of the HAC per mole of the water. For example, the proportion of reactants may be from a minimum of about 0.5, 1.0, 2.0, 3.0, 4.0, 5.0, 6.0, or 7.0 to a maximum of 1.0, 2.0, 3.0, 4.0, 5.0, 6.0, 7.0, or 8.0 moles of the HAC per mole of the water. The proportions may be from about 1.3 to about 6.0 or from about 2.0 to about 4.0 moles of the HAC per mole of the water.

The reaction temperature for the hydrolysis reaction of the HAC may be from about −70° C. to about 100° C., or from about −50° C. to about 50° C., or from about −20° C. to about 20° C. The hydrolysis reaction for production of the aluminoxane can be continuous or in batches, as desired for particular applications. Where the aluminoxane production is in batches, embodiments may include intermediate storage of the product aluminoxane and recycled solvent. In some embodiments, the production of aluminoxane may be integrated into a continuous flow process for catalyst production.

The concentration of aluminoxane in the solvent may be controlled by adjustment of the reactant feed rates and/or the product removal rates among others. The aluminoxane concentration in the solvent may be from about 2% to about 40%, by weight. For example, the aluminoxane concentration in the solvent may be from a minimum of about 2%, 5%, 10%, 15%, 20%, 25%, 30%, or 35% to a maximum of about 5%, 10%, 15%, 20%, 25%, 30%, 35%, or 40%, by weight. In some embodiments, the aluminoxane concentration in the solvent may be from about 20% to about 30%, by weight. The aluminoxane concentration in the solvent may also be less than about 10%, by weight, or in a range of from about 2% to about 10%, by weight. The concentration of unreacted HAC in the solvent may vary and, in some embodiments, may range from about 1% to about 5%, by weight.

The product aluminoxane from this hydrolysis reaction in solvent, which contains unreacted HAC, may be removed and combined with catalyst component(s) to form a catalyst feedstock comprising a catalyst composition. Non-limiting examples of catalyst components that may be used comprise metallocene catalysts, conventional catalysts such as Ziegler-Natta catalysts and Phillips-type chromium catalysts, and Group 15-containing catalysts. Also contemplated are catalysts such as $AlCl_3$, cobalt, iron, and palladium catalysts. In addition to the catalyst component, the aluminoxane may also be combined with a support and/or a continuity additive. Non-limiting examples of suitable supports include inorganic or organic support materials, which may be a porous support material, for example. Examples of suitable catalyst components, supports, and continuity additives will be described in more detail below.

The aluminoxane and catalyst component(s) may be contacted for at least about 0.1 minutes. In some embodiments, the aluminoxane and catalyst components may be contacted for between 0.1 minutes and 10,000 minutes, or between about 1 minute and 1440 minutes, or between about 5 minutes and 240 minutes. The aluminoxane may be present at a molar ratio of about 10,000:1 to about 0.5:1 of the Al of the aluminoxane to the metal of the catalyst, or at a molar ratio of about 500:1 to about 10:1, or at a molar ratio of about 400:1 to about 20:1, or at a molar ratio of about 300:1 to about 30:1.

After combination of the aluminoxane with the catalyst components to form a catalyst feedstock comprising the catalyst composition, embodiments may include separation of the catalyst composition from the remainder of the catalyst feedstock (including, for example, the solvent and the unreacted HAC). Any suitable technique for separation or isolation of the formed catalyst composition may be used. For example, the catalyst feedstock may be dried to form a powder by removal of the more volatile components, including the solvent and the unreacted HAC, for example. The catalyst feedstock may be dried by any suitable technique, including heat, vacuum, heat and vacuum in a batch process, or spray drying, for example, to remove the liquids. In some embodiments, the catalyst composition may comprise the catalyst complex being deposited on or in the support, for example, the catalyst complex may be adsorbed or absorbed in, or on the support. In some embodiments, the powder may be free flowing. The gaseous mixture of the solvent and unreacted HAC removed from the catalyst composition may be condensed, collected, and recycled for reuse in production of aluminoxane.

In particular embodiments, upon mixing/reaction of the aluminoxane and catalyst component(s), the catalyst feedstock (including, for example, the aluminoxane, catalyst, support, and/or unreacted HAC in solvent) may be spray dried, in which a fine mist of the catalyst feedstock may be rapidly dried by contact with hot nitrogen or other inert gas stream. In some embodiments, the hot nitrogen meets the catalyst feedstock at an atomizer, which produces a droplet stream on a continuous basis. Dried catalyst particles are trapped out of the process in a separator, such as a cyclone, which can separate solids formed from a gaseous mixture of the nitrogen, solvent, and volatile components, such as the unreacted HAC. The gaseous mixture may be sent to a condenser, where the solvent, unreacted HAC, other organic components, and catalyst fines may be condensed out of the gaseous nitrogen phase by contact, for example, with a countercurrent condensing column at low temperatures, e.g., about −5° C. The cold gaseous stream containing essentially all of the nitrogen may be reheated and cycled back to the atomizer for spray drying of additional catalyst feedstock. The liquids collected may be recycled back for preparation of additional aluminoxanes.

Turning now to the figures, example embodiments for integration of aluminoxane production into production of catalyst compositions will now be described in conjunction with FIGS. 1-5. It should be understood that the specific arrangements shown on FIGS. 1-5 are merely exemplary and modifications may be made to the illustrated embodiments while keeping with the scope and spirit of the disclosed embodiments.

FIG. 1 illustrates a catalyst production system 5 in accordance with embodiments disclosed herein. As illustrated, the catalyst production system 5 may comprise an aluminoxane production unit 10, a catalyst mixing unit 15, a drying unit 20, and a vapor condensation unit 25. A recycle stream 30 may be fed into reactor loop 35 in the aluminoxane production unit 10. The recycle stream 30 generally may comprise a solvent and HAC. A water stream 40 and an HAC stream 45 may also be fed to the reactor loop 35. In some embodiments, the recycle stream 30, water stream 40, and HAC stream 45, or one or more of these streams, may be continuously injected into the inlet of an inline mixer (not shown). The inline mixer may, for example, provide a homogenous reaction zone. Additionally, one or more of these streams may be injected into the reactor loop 35 at a different point.

In the reactor loop 35, the water and HAC may react to form a reaction mixture comprising an alkane (e.g., methane), product aluminoxane, and unreacted HAC. The reaction mixture may be circulated in the reactor loop 35 to degassing tank 50 where byproduct methane formed in the hydrolysis reaction may be removed via gas stream 55, for example. A make-up solvent stream 60 may also be added to the aluminoxane production unit 10. As illustrated, the make-up solvent stream 60 may be added to the degassing tank 50 to account for loss of the solvent with the gas stream 55 and in the dried catalyst composition 90, for example. A pump 65 may be used for circulation of the reaction mixture in the reactor loop 35. The reaction mixture may pass through a cooler 70, for example, to maintain the hydrolysis reaction in a selected temperature range. As illustrated, a portion of the reaction mixture may be pumped around the reactor loop 35. The pumped around portion of the reaction mixture may be fed to the inlet of the inline mixer (not shown). In addition, a product stream 75 comprising product aluminoxane in solvent, which contains some unreacted HAC may be withdrawn from reactor loop 35.

The product stream 75 may be withdrawn from the reactor loop 35 and mixed with additional catalyst components 80 in catalyst mixing unit 15 to form a catalyst feedstock 85. The additional catalyst components 80 may comprise catalyst components and/or supports, and/or continuity additives, for example. The product stream 75 may comprise aluminoxane in solvent together with some unreacted HAC. The aluminoxane and catalyst components may react or otherwise combine to form a catalyst composition. A drying unit 20 may be used to separate the catalyst composition from the more volatile components, such as the solvent and the unreacted HAC. The drying unit 20 may include heating, vacuuming, and/or spray drying of the catalyst feedstock 85. In the drying unit 20, the dried catalyst composition 90 may be collected, for example, in a powder form. A gaseous mixture 95 comprising the solvent and other volatiles (e.g., the unreacted HAC) may also be removed from the drying unit 20. In spray-drying embodiments, the gaseous mixture 95 may further comprise nitrogen gas which may be used in the spray drying of the catalyst feedstock 85. A condensing unit 25 may be used for condensing the solvent with the recycle stream 30 comprising the solvent and unreacted HAC being recycled to the aluminoxane production unit 10. Nitrogen gas, if any, may also be separated from the solvent in the condensing unit 25 for reuse in spray drying. As illustrated, solvent waste stream 26 may also be removed from condensing unit 25. It is contemplated that embodiments may include removal of at least a portion of the solvent or other liquids from system 5 via solvent waste stream 26 and not recycled to the aluminoxane production unit 10.

Figure 2:
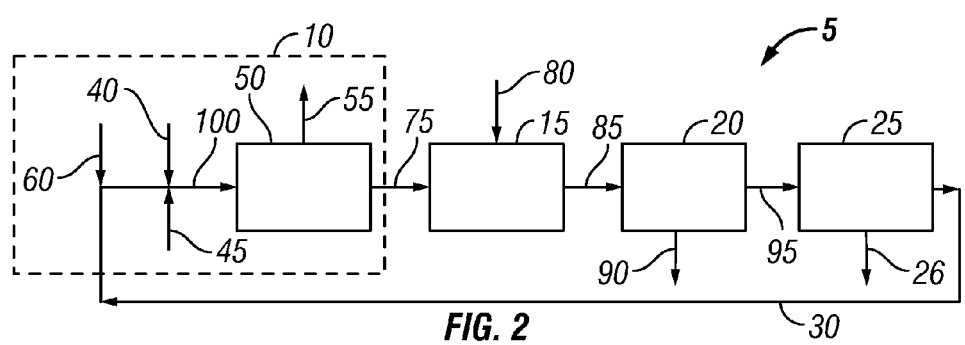
FIG. 2 is a schematic diagram illustrating another example method for catalyst production that includes integrated aluminoxane production.

Referring now to FIG. 2, another embodiment of a catalyst production system 5 is illustrated in which the aluminoxane production unit 10 does not include pump around of the reaction mixture. Without being limited by theory, pump around may not be needed as the alumoxane in the product stream 75 may not be concentrated and can be used at concentrations of less than about 10% by weight of alumoxane. As illustrated, the recycle stream 30 comprising solvent and HAC may be recycled and combined with a water stream 40 and the HAC stream 45 to form a reaction stream 100. In the reaction stream 100, the water and HAC may react to form a reaction mixture comprising solvent, product aluminoxane, and unreacted HAC. A degassing tank 50 may be used to remove byproduct methane from the reaction stream 100 via gas stream 55. A make-up solvent stream 60 may also be added to the aluminoxane production unit 10. As illustrated, the make-up solvent stream 60 may be added to the recycle stream 30. A product stream 75 comprising product aluminoxane in solvent, which contains unreacted HAC may be fed to the catalyst mixing unit 15 and mixed with additional catalyst components 80 to form a catalyst feedstock 85. The aluminoxane and catalyst components may react or otherwise combine to form a catalyst composition. A drying unit 20 may be used to separate the catalyst composition from the more volatile components in the catalyst feedstock 85, such as the solvent and the unreacted HAC. In the drying unit 20, the dried catalyst composition 90 may be collected, for example, in a powder form. A gaseous mixture 95 comprising the solvent and other volatiles (e.g., the unreacted HAC) may also be removed from the drying unit 20. A condensing unit 25 may be used for condensing the solvent with the recycle stream 30 comprising the solvent and unreacted HAC being recycled to the aluminoxane production unit 10. Solvent waste stream 26 may also be removed from condensing unit 25.

Figure 3:
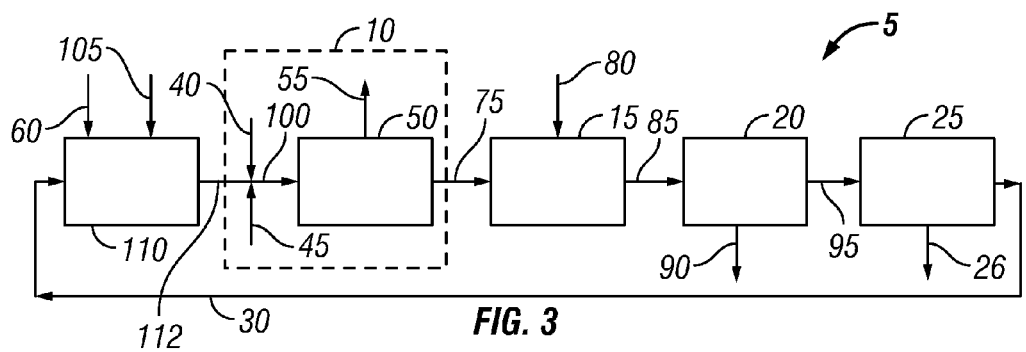
FIG. 3 is a schematic diagram illustrating yet another example method for catalyst production that includes integrated aluminoxane production, wherein a catalyst support is introduced into the system before conversion of the trialkylaluminum compound to an aluminoxane.

Referring now to FIG. 3, another embodiment of a catalyst production system 5 is illustrated in which support material 105 is added prior to the aluminoxane production unit 10. Without being limited by theory, alumoxane distribution on the support material 105 may be improved by introducing the support material 105 prior to the aluminoxane production unit 10. In some embodiments, the support material 105 may be a wet support material, such as wet silica, having some water content. In addition, temperature rise from the hydrolysis reaction in the aluminoxane production unit 10 may also be lessened due to presence of the support material 105. As illustrated, the recycle stream 30 comprising solvent and HAC may be recycled and combined with the support material 105 in support mixing unit 110. As illustrated, a make-up solvent stream 60 may also be added to the support mixing unit 110. A support/recycle mixture 112 from the support mixing unit 110 may be fed to the aluminoxane production unit 10 and combined with a water stream 40 and the HAC stream 45 to form a reaction stream 100. All or a portion of the HAC stream 45 could also be fed to the support mixing unit 110. Some or all of the water stream 40 may also be introduced before addition of the support material 105 or just upstream of the additional catalyst components 80. In the reaction stream 100, the water and HAC may react to form a reaction mixture comprising solvent, product aluminoxane, and unreacted HAC. A degassing tank 50 may be used to remove byproduct methane from the reaction stream 100 via gas stream 55. A product stream 75 comprising product aluminoxane in solvent, which contains unreacted HAC may be fed to the catalyst mixing unit 15 and mixed with additional catalyst components 80 to form a catalyst feedstock 85. The aluminoxane and catalyst components may react or otherwise combine to form a catalyst composition. A drying unit 20 may be used to separate the catalyst composition from the more volatile components in the catalyst feedstock 85, such as the solvent and the unreacted HAC. In the drying unit 20, the dried catalyst composition 90 may be collected, for example, in a powder form. A gaseous mixture 95 comprising the solvent and other volatiles (e.g., the unreacted HAC) may also be removed from the drying unit 20. A condensing unit 25 may be used for condensing the solvent with the recycle stream 30 comprising the solvent and unreacted HAC being recycled to the aluminoxane production unit 10. Solvent waste stream 26 may also be removed from condensing unit 25.

Figure 4:
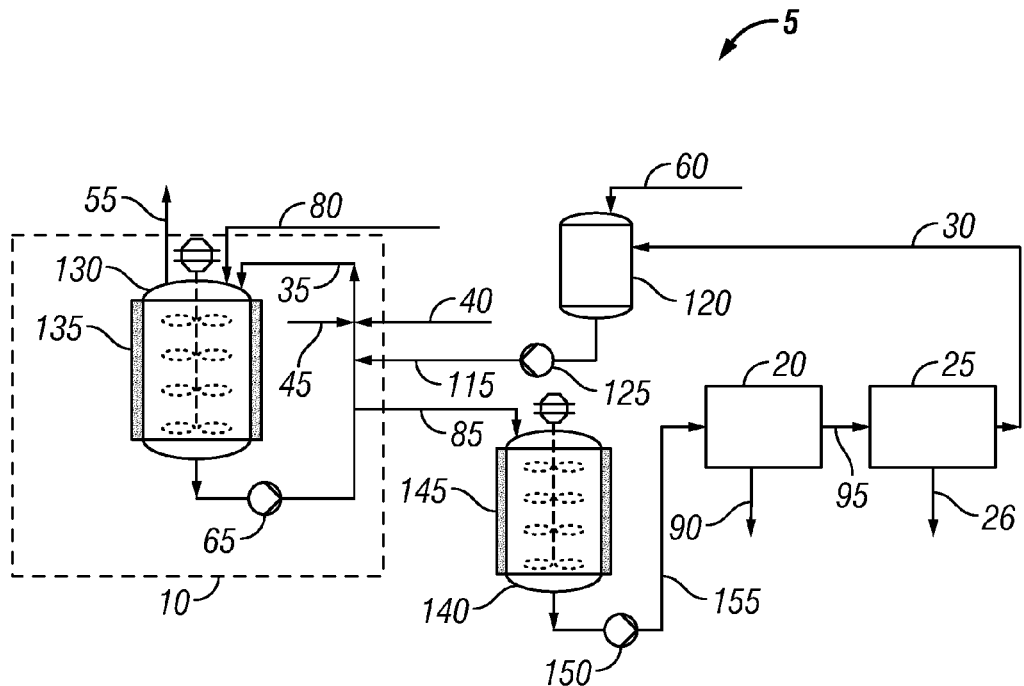
FIG. 4 is a schematic diagram illustrating yet another example method for catalyst production that includes integrated aluminoxane production, wherein the catalyst mixing tank and degassing vessel have been combined.

Referring now to FIG. 4, yet another embodiment of a catalyst production system 5 is illustrated. In the illustrated embodiment, the catalyst mixing unit 15 and the degassing tank 50 of FIGS. 1-3 have been combined in the aluminoxane production unit 10. In some embodiments, the aluminoxane production unit 10 in the catalyst production system 5 of FIG. 4 may be operated in a batch made to produce aluminoxane. In one particular embodiment, recycled solvent with HAC may be fed into the aluminoxane production unit 10 via line 115. The recycled solvent may be fed from a recycle surge vessel 120 via pump 125. As illustrated, a make-up solvent stream 60 may be added to the recycle surge vessel 120.

The recycled solvent may be circulated in the reactor loop 35 in the aluminoxane production unit 10. In some embodiments, support material (not shown) may now be introduced into the reactor loop 35. Without being limited by theory, introduction of the support material may help absorb the heat of the hydrolysis reaction and could also affect integration of the aluminoxane onto the support material. A cooling jacket (not shown) could also be used to remove the heat of reaction. To produce product aluminoxane, the water stream 40 and HAC stream 45 may also be fed to the reactor loop 35. In the reactor loop 35, the water and HAC may react to form a reaction mixture comprising solvent, product aluminoxane, and unreacted HAC. Degassing/catalyst mix tank 130 in the reactor loop 35 may remove byproduct methane from the reaction mixture via gas stream 55, which may be sent to flare, for example. A pump 65 may be used for circulation of the reaction mixture in the reactor loop 35.

The injection of the water stream 40 and the HAC stream 45 may then be ceased and additional catalyst components 80 may then be introduced into the degassing/catalyst mix tank 130, for example. The additional catalyst components 80 may comprise catalyst components, supports, and/or continuity additives, for example. A heating jacket 135 on the degassing/catalyst mix tank 130 may be used, for example, to increase system temperature. The produced aluminoxane and catalyst components may react or otherwise combine to form a catalyst composition.

A catalyst feedstock 85 comprising the catalyst composition, solvent, and unreacted HAC may then be removed from the aluminoxane production unit 10 and fed to a surge vessel 140, which may include a heating jacket 145, for example. From the catalyst surge vessel 140, a pump 150 may be used to deliver a stream 155 comprising the catalyst composition, solvent, and unreacted HAC to the drying unit 20 via line 155. The drying unit 20 may be integrated into the degassing/catalyst mix tank 130. The drying unit 20 may be used to separate the catalyst composition from the more volatile components, such as the solvent and the unreacted HAC. In the drying unit 20, the dried catalyst composition 90 may be collected, for example, in a powder form. A gaseous mixture 95 comprising the solvent and other volatiles (e.g., the unreacted HAC) may also be removed from the drying unit 20. A condensing unit 25 may be used for condensing the solvent with the recycle stream 30 comprising the solvent and unreacted HAC being recycled to the recycle surge vessel 120. Solvent waste stream 26 may also be removed from condensing unit 25.

Figure 5:
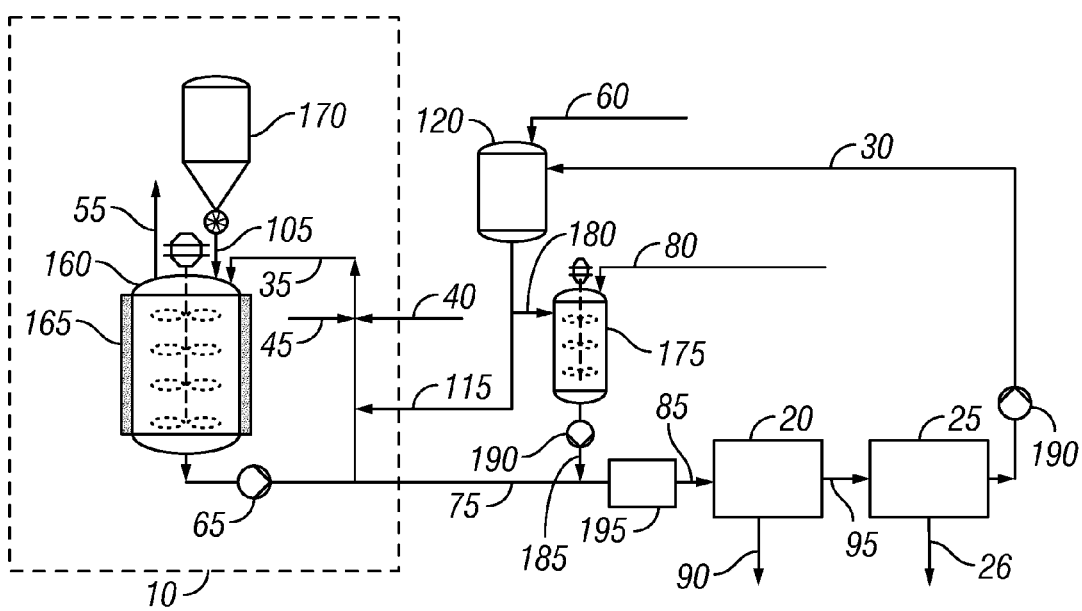
FIG. 5 is a schematic diagram illustrating yet another example method for catalyst production.

Referring now to FIG. 5, another embodiment of a catalyst production system 5 is illustrated. In the illustrated embodiment, recycled solvent with HAC may be fed from a recycle surge vessel 120 into the aluminoxane production unit 10 via line 115. Recycled solvent with HAC, line 115, may also be fed to the degassing/mix tank 160 (embodiment now shown). As illustrated, a make-up solvent stream 60 may be added to the recycle surge vessel 120. The recycled solvent may be circulated in the reactor loop 35 in the aluminoxane production unit 10. To produce product aluminoxane, the water stream 40 and HAC stream 45 may also be fed to the reactor loop 35. In the reactor loop 35, the water and HAC may react to form a reaction mixture comprising solvent, product aluminoxane, and unreacted HAC. Degassing/support mix tank 160 in the reactor loop 35 may remove byproduct methane from the reaction mixture via gas stream 55, which may be sent to flare, for example. The degassing/support mix tank 160 may include a jacket 165 for temperature control, which may be a heating or cooling jacket, for example. A pump 65 may be used for circulation of the reaction mixture in the reactor loop 35. In some embodiments, support material 105 may also be introduced into the reactor loop 35. Without being limited by theory, introduction of the support material 105 may help absorb the heat of the hydrolysis reaction and could also effect integration of the aluminoxane onto the support material. In some embodiments, the support material 105 may be a wet support material, such as wet silica, having some water content. As illustrated, the support material 105 may be introduced into the degassing/support mix tank 160 from support surge hopper 170. As illustrated, a portion of the reaction mixture may be pumped around the reactor loop 35. In addition, a product stream 75 comprising product aluminoxane in solvent, which contains some unreacted HAC and support material, may be withdrawn from reactor loop 35.

As illustrated, additional catalyst components 80 may be fed into a catalyst component mix tank 175. A side stream 180 of the recycled solvent (including, for example, some unreacted HAC) from the recycle surge tank 120 may also be fed to the catalyst component mix tank 175. The catalyst components 185 which include the recycled solvent from the side stream 180 may be withdrawn from the catalyst component mix tank 175 and combined with the product stream 75. As illustrated, the catalyst components 185 and the product stream 75 may be introduced into the inlet of an inline mixer 195, for example, in which they are combined to form a catalyst feedstock 85. Pump 190 may be used to deliver the catalyst components 185 to the inline mixer 195. The aluminoxane and catalyst components may react or otherwise combine to form a catalyst composition. A drying unit 20 may be used to separate the catalyst composition from the more volatile components in the catalyst feedstock 85, such as the solvent and the unreacted HAC. In the drying unit 20, the dried catalyst composition 90 may be collected, for example, in a powder form. A gaseous mixture 95 comprising the solvent and other volatiles (e.g., the unreacted HAC) may also be removed from the drying unit 20. A condensing unit 25 may be used for condensing the solvent with the recycle stream 30 comprising the solvent and unreacted HAC being recycled to the aluminoxane production unit 10 via pump 190. Solvent waste stream 26 may also be removed from condensing unit 25.

Catalyst Component

The catalyst component may be combined with the aluminoxane. Non-limiting examples of catalyst components that may be used comprise metallocene catalysts, conventional catalysts such as Ziegler-Natta catalysts and Phillips-type chromium catalysts, and Group 15-containing catalysts. Also contemplated are catalysts such as $AlCl_3$, cobalt, iron, and palladium catalysts. The term "catalyst component," as used herein, is used interchangeably with the term "catalyst," and includes any compound or component, or combination of compounds and components, that is capable of increasing the rate of a chemical reaction, such as the polymerization or oligomerization of one or more olefins. In some embodiments, the catalyst component may be a single-site catalyst.

Metallocene Catalysts

Suitable catalyst components may comprise metallocene catalysts. Metallocene or metallocene-type catalyst compounds generally contain one or more ligands including cyclopentadienyl (Cp) or cyclopentadienyl-type structures or other similar functioning structure such as pentadiene, cyclooctatetraendiyl, and imides. It is understood by one of skill in the art that references made herein to metallocene catalyst compounds and/or systems may also refer to metallocene-type catalyst compounds and/or compositions. As used herein, a catalyst composition refers to a combination comprising a catalyst compound and a cocatalyst or activator. Typical metallocene compounds are generally described as containing one or more ligand(s) and one or more leaving group(s) bonded to at least one metal atom. For the purposes herein, the term "leaving group" may refer to one or more chemical moieties, such as a ligand, bound to the center metal atom of a catalyst component that can be abstracted from the catalyst component by an activator or cocatalyst, thus producing a catalyst species active toward olefin polymerization or oligomerization. Examples of these metallocene catalyst compounds and catalyst compositions are described in, for example, U.S. Pat. Nos. 4,530,914, 4,871,705, 4,937,299, 5,017,714, 5,055,438, 5,096,867, 5,120,867, 5,124,418, 5,198,401, 5,210,352, 5,229,478, 5,264,405, 5,278,264, 5,278,119, 5,304,614, 5,324,800, 5,347,025, 5,350,723, 5,384,299, 5,391,790, 5,391,789, 5,399,636, 5,408,017, 5,491,207, 5,455,366, 5,534,473, 5,539,124, 5,554,775, 5,621,126, 5,684,098, 5,693,730, 5,698,634, 5,710,297, 5,712,354, 5,714,427, 5,714,555, 5,728,641, 5,728,839, 5,753,577, 5,767,209, 5,770,753 and 5,770,664. Also, the disclosures of European publications such as EP-A-0 591 756, EP-A-0 520 732, EP-A-0 420 436, EP-B1 0 485 822, EP-B1 0 485 823, EP-A2-0 743 324 and EP-B1 0 518 092 and PCT publications WO 91/04257, WO 92/00333, WO 93/08221, WO 93/08199, WO 94/01471, WO 96/20233, WO 97/15582, WO 97/19959, WO 97/46567, WO 98/01455, WO 98/06759, and WO 98/011144 describe typical metallocene catalyst compounds and catalyst compositions.

The Cp ligands are generally one or more open, acyclic, or fused ring(s) or rings system(s) or a combination thereof At least a portion of the Cp ligands may include π-bonded systems, such as cycloalkadienyl ligands and heterocyclic analogues. The ring(s) or ring system(s) typically comprise atoms selected from Groups 13 to 16 atoms, and, in some embodiments, the atoms that make up the Cp ligands are selected from carbon, nitrogen, oxygen, silicon, sulfur, phosphorous, germanium, boron, aluminum, and combinations thereof, where carbon makes up at least 50% of the ring members. In some embodiments, the Cp ligand(s) are selected from substituted and unsubstituted cyclopentadienyl ligands and ligands isolobal to cyclopentadienyl. Non-limiting examples of such ligands include cyclopentadienyl, cyclopentaphenanthrenyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$ Ind"), substituted versions thereof (as discussed and described in more detail below), and heterocyclic versions thereof.

The metal atom "M" of the metallocene compound may be selected from Groups 3 through 12 atoms and lanthanide Group atoms; or may be selected from Groups 3 through 10 atoms; or may be selected from Sc, Ti, Zr, Hf, V, Nb, Ta, Mn, Re, Fe, Ru, Os, Co, Rh, Ir, and Ni; or may be selected from Groups 4, 5, and 6 atoms; or may be Ti, Zr, or Hf atoms; or may be Hf; or may be Zr. The oxidation state of the metal atom "M" can range from 0 to +7; or may be +1, +2, +3, +4 or +5; or may be +2, +3 or +4. The groups bound to the metal atom "M" are such that the compounds described below in the structures and structures are electrically neutral, unless otherwise indicated. The Cp ligand(s) forms at least one chemical bond with the metal atom M to form the "metallocene catalyst component." The Cp ligands are distinct from the leaving groups bound to metal atom M in that they are not highly susceptible to substitution/abstraction reactions.

The metallocene catalyst component may include compounds represented by Structure (I):

Cp$^A$Cp$^B$MX$_n$                                   (I)

where M is as described above; each X is chemically bonded to M; each Cp group is chemically bonded to M; and n is 0 or an integer from 1 to 4. In some embodiments, n is either 1 or 2.

The ligands represented by Cp$^A$ and Cp$^B$ in Structure (I) may be the same or different cyclopentadienyl ligands or ligands isolobal to cyclopentadienyl, either or both of which may contain heteroatoms and either or both of which may be substituted by a group R. For example, Cp$^A$ and Cp$^B$ may be independently selected from cyclopentadienyl, indenyl, tetrahydroindenyl, fluorenyl, and substituted derivatives of each.

Independently, each Cp$^A$ and Cp$^B$ of Structure (I) may be unsubstituted or substituted with any one or combination of substituent groups R. Non-limiting examples of substituent groups R as used in Structure (I) include hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyl thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof More particular non-limiting examples of alkyl substituents R associated with Structure (I) include methyl, ethyl, propyl, butyl, pentyl, hexyl, cyclopentyl, cyclohexyl, benzyl, phenyl, methylphenyl, and tert-butylphenyl groups and the like, including all their isomers, for example tertiarybutyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins, such as, but not limited to, olefinically unsaturated substituents including vinyl-terminated ligands, for example 3-butenyl, 2-propenyl, 5-hexenyl, and the like. In some embodiments, at least two R groups, for example, two adjacent R groups, are joined to form a ring structure having from 3 to 30 atoms selected from carbon, nitrogen, oxygen, phosphorous, silicon, germanium, aluminum, boron and combinations thereof Also, a substituent R group, such as 1-butanyl, may form a bonding association to the element M.

Each X in Structure (I), above, and Structures (II), below, is independently selected from: for example, halogen ions, hydrides, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof In some embodiments, X is a $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, or $C_1$ to $C_{12}$ heteroatom-containing hydrocarbons, and substituted derivatives thereof X may be selected from hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_i$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, or $C_7$ to $C_{18}$ fluoroalkylaryls; or X may be selected from hydride, chloride, fluoride, methyl, phenyl, phenoxy, benzoxy, tosyl, fluoromethyls, and fluorophenyls; or X may be selected from $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls; or X may be selected from chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls; or X may be selected from fluoride, methyl, ethyl, propyl, phenyl, methylphenyl, dimethylphenyl, trimethylphenyl, fluoromethyls (mono-, di- and trifluoromethyls), and fluorophenyls (mono-, di-, tri-, tetra- and pentafluorophenyls). In some embodiments, at least one X is a halogenated aryloxy group or a derivative thereof For example, at least one X may be a pentafluorophenoxy group.

The metallocene catalyst component may include those metallocenes of Structure (I) where $Cp^A$ and $Cp^B$ are bridged to each other by at least one bridging group, (A), such that the structure is represented by Structure (II):

$$Cp^A(A)Cp^B MX_n \qquad (II)$$

These bridged compounds represented by Structure (II) are known as "bridged metallocenes." $Cp^A$, $Cp^B$, M, X and n in Structure (II) are as defined above for Structure (I); and wherein each Cp ligand is chemically bonded to M, and (A) is chemically bonded to each Cp. Non-limiting examples of bridging group (A) include divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, and divalent thioethers. Additional non-limiting examples of bridging group A include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above for Structure (I) including halogen radicals and iron. More particular non-limiting examples of bridging group (A) are represented by $C_1$ to $C_6$ alkylenes, substituted $C_1$ to $C_6$ alkylenes, oxygen, sulfur, $R'_2C=$, $R'_2Si=$, $-Si(R')_2Si(R'_2)-$, $R'_2Ge=$, $R'P=$ (wherein "=" represents two chemical bonds), where R' is independently selected from hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In some embodiments, the bridged metallocene catalyst component of Structure (II) has two or more bridging groups (A).

Other non-limiting examples of bridging group (A), in Structure (II), include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In some embodiments, bridging group (A), in Structure (II), may also be cyclic, comprising, 4 to 10 ring members or 5 to 7 ring members. The ring members may be selected from the elements mentioned above, or from one or more of B, C, Si, Ge, N and O. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination thereof.

The cyclic bridging groups (A) may be saturated or unsaturated and/or carry one or more substituents and/or be fused to one or more other ring structures. If present, the one or more substituents may be a hydrocarbyl (e.g., alkyl such as methyl) or halogen (e.g., F, Cl). The one or more Cp groups which the above cyclic bridging moieties may optionally be fused to may be saturated or unsaturated and are selected from those having 4 to 10, more particularly 5, 6, or 7 ring members (selected from C, N, O and S in a particular embodiment), such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

It is also contemplated that, the metallocene catalysts may include their structural or optical or enantiomeric isomers (meso and racemic isomers) and mixtures thereof. In some embodiments, the metallocene compounds may be chiral and/or a bridged metallocene catalyst compound. Further, as used herein, a single, bridged, asymmetrically substituted metallocene catalyst component having a racemic and/or meso isomer does not, itself, constitute at least two different bridged, metallocene catalyst components.

Conventional Catalysts

Conventional catalysts are traditional Ziegler-Natta catalysts and Phillips-type chromium catalysts known in the art. Traditional Ziegler-Natta catalysts are those conventional-type transition metal catalysts that are well known in the art. Examples of conventional-type transition metal catalysts are disclosed in U.S. Pat. Nos. 4,115,639, 4,077,904 4,482,687, 4,564,605, 4,721,763, 4,879,359 and 4,960,741. Conventional-type transition metal catalyst compounds that may be used include, but are not limited to, transition metal compounds from Groups III to VIII of the Periodic Table of the Elements. Reference in this section to the Periodic Table of the Elements refers to the Periodic Table of the Elements, published and copyrighted by the International Union of Pure and Applied Chemistry, Inc., 2004. Also, any reference to a Group or Groups shall be to the Group or Groups as reflected in this Periodic Table of the Elements using the IUPAC system for numbering groups.

These conventional-type transition metal catalysts may be represented by the formula: $MR_x$, where M is a metal from Groups IIIB to VIII, preferably Group IVB, more preferably titanium; R is a halogen or a hydrocarbyloxy group; and x is the valence of the metal M. Non-limiting examples of R may include alkoxy, phenoxy, bromide, chloride and fluoride. Conventional-type transition metal catalysts where M is titanium may include, but are not limited to, $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3.1/3AlCl_3$ and $Ti(OC_{12}H_{25})Cl_3$.

Other suitable catalysts are described in, U.S. Pat. Nos. 4,302,565 and 4,302,566 and in British Patent Application 2,105,355.

Conventional-type chromium catalyst compounds, often referred to as Phillips-type catalysts, suitable for use may include $CrO_3$, chromocene, silyl chromate, chromyl chloride ($CrO_2Cl_2$), chromium-2-ethyl-hexanoate, chromium acetylacetonate ($Cr(AcAc)_3$), and the like. Non-limiting examples are disclosed in U.S. Pat. Nos. 3,242,099 and 3,231,550.

Still other conventional-type transition metal catalyst compounds and catalyst compositions suitable for use include those disclosed in U.S. Pat. Nos. 4,124,532, 4,302,565, 4,302,566 and 5,763,723 and EP Publications EP-A2 0 416 815 and EP-A10 420 436.

Conventional-type cocatalyst compounds for the above described conventional-type transition metal catalyst compounds may be represented by the formula $M^3M^4_vX^2_cR^3_{b-c}$, wherein $M^3$ is a metal from Group IA, IIA, IIB and IIIA of the Periodic Table of Elements; $M^4$ is a metal of Group IA of the Periodic Table of Elements; v is a number from 0 to 1; each $X^2$ is any halogen; c is a number from 0 to 3; each $R^3$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula $M^3R^3_k$, where $M^3$ is a Group IA, IIA, IIB or IIIA metal, such as lithium, sodium, beryllium, barium, boron, aluminum, zinc, cadmium, and gallium; k equals 1, 2 or 3 depending upon the valency of M.sup.3 which valency in turn normally depends upon the particular Group to which $M^3$ belongs; and each $R^3$ may be any monovalent hydrocarbon radical.

Group 15 Atom and Metal Containing Catalysts

In some embodiments, "Group 15 atom and metal-containing catalysts," or the short-hand "Group 15-containing" catalyst, may be used either alone or with a metallocene or other olefin polymerization catalyst. Generally, Group 15-containing catalyst components may include complexes of Group 3 to 12 metal atoms, wherein the metal atom is 2 to 8 coordinate, the coordinating moiety or moieties including at least two Group 15 atoms, and up to four Group 15 atoms. In one embodiment, the Group 15-containing catalyst component is a complex of a Group 4 metal and from one to four ligands such that the Group 4 metal is at least 2 coordinate, the coordinating moiety or moieties including at least two nitrogens. Representative Group 15-containing compounds are disclosed in, for example, WO 99/01460, EP Al 0 893 454, U.S. Pat. Nos. 5,318,935, 5,889,128, 6,333,389 B2 and 6,271,325 B1.

In some embodiments, the Group 15-containing catalyst components may include Group 4 imino-phenol complexes, Group 4 bis(amide) complexes, and Group 4 pyridyl-amide complexes that are active towards olefin polymerization to any extent. In one possible embodiment, the Group 15-containing catalyst component may include a bisamide compound such as $[(2,3,4,5,6\ Me_5C_6)NCH_2CH_2]_2NHZrBz_2$.

Mixed Catalysts

In some embodiments, a mixed catalyst may be used. A mixed catalyst includes a combination of two or more of catalyst components. In an embodiment, one or more metallocene catalysts or catalyst compositions may be combined with one or more conventional-type catalysts or catalyst compositions. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010. It is further contemplated that two or more conventional-type transition metal catalysts may be combined with one or more conventional-type cocatalysts. Non-limiting examples of mixed conventional-type transition metal catalysts are described in for example U.S. Pat. Nos. 4,154,701, 4,210,559, 4,263,422, 4,672,096, 4,918,038, 5,198,400, 5,237,025, 5,408,015 and 5,420,090.

Supported Catalysts

In some embodiments, the catalyst may be supported. For example, each component of the catalyst composition (including, for example, the catalyst and the aluminoxane) may be supported on a support. As used herein, the term "supported" refers to one or more compounds that are deposited on, contacted with, vaporized with, adsorbed or absorbed in, or on, a support or carrier. The terms "support" and "carrier," for the purposes of this specification, are used interchangeably and are any support material, such as a porous support material, including inorganic or organic support materials.

Non-limiting examples of suitable supports include compounds comprising Groups 2, 3, 4, 5, 13 and 14 oxides and chlorides. Suitable supports may include, for example, silica, magnesia, titania, zirconia, montmorillonite, phyllosilicate, alumina, silica-alumina, silica-chromium, silica-titania, magnesium chloride, graphite, magnesia, titania, zirconia, montmorillonite, phyllosilicate, and the like. Combinations of supports may also be suitable, including, for example, silica-chromium, silica-alumina, silica-titania, and the like. In one embodiment, fumed silica is a suitable support.

The support may possess an average particle size in the range of from about 0.1 to about 90 µm, or from about 1 to about 40 µm, or from about 5 to about 40 µm.

The support, such as an inorganic oxide, may have a surface area in the range of from about 10 to about 700 m²/g, a pore volume in the range of from about 0.1 to about 4.0 cc/g, and an average particle size in the range of from about 1 to about 500 µm. In some embodiments, the support may have a surface area in the range of from about 50 to about 500 m²/g, a pore volume of from about 0.5 to about 3.5 cc/g, and an average particle size of from about 10 to about 200 µm. In some embodiments, the support may have a surface area in the range of from about 100 to about 400 m²/g, a pore volume from about 0.8 to about 3.0 cc/g, and an average particle size is from about 5 to about 100 µpm. In some embodiments, the average pore size of the support may be from about 1 to about 50 µm. In some embodiments, the average pore size of the support may be in the range of from about 10 to about 1000 Å, of from about 50 to about 500 Å, or from about 75 to about 350 Å.

The catalyst components may be supported on the same or separate supports together with an activator, or the activator may be used in an unsupported form, or may be deposited on a support different from the supported catalyst components, or any combination thereof As previously described, spray-drying may be used for combining the catalyst components with the one or more supports. Spray-drying of a catalyst or catalyst composition may result in catalyst or catalyst compositions having increased catalyst productivity as compared to other techniques for catalyst preparation. Example techniques for spray-drying a catalyst or catalyst composition are described, for example, in U.S. Pat. Nos. 5,648,310; 5,674,795; and 5,672,669, and EP0668295 B1.

The catalysts and/or activators(s) may be combined with a particulate support material and then spray-dried, for example, to form a free flowing powder. By way of example, the catalyst and optionally the activator(s) may be placed in solution, allowing them to react, then adding a filler material, such as silica or Cabosil™, and then forcing the solution at high pressure through a nozzle. The solution may be sprayed onto a surface or sprayed such that the droplets dry in midair. In some embodiments, the filler material (such as silica) may be dispersed in toluene or another suitable solvent, then stir in the activator solution, and then stir in the catalyst components. Typical slurry concentrations are about 5-8 wt %, for example. This formulation may sit as a slurry for as long as 30 minutes with mild stirring or manual shaking to keep it as a suspension before spray-drying. In some embodiments, the makeup of the dried material may be about 40-50 wt % activator (e.g., alumoxane), about 50-60 wt % filler material (e.g., $SiO_2$), and about 2 wt % catalyst components.

In some embodiments, the catalyst components can be added together in the desired ratio in the last step. In some embodiments, more complex procedures are possible, such as addition of a first catalyst component to the activator/filler material for a specified reaction time, followed by addition of a second catalyst component, mixed for another specified reaction time, after which the mixture is co-sprayed. For example, an additive, such as 1-hexene (e.g., about 10 vol %), may be present in the activator/filler mixture prior to addition of the first catalyst component.

In some embodiments, binders may be added to the mix. For example, the binders can be added as a means of improving the particle morphology, i.e. narrowing the particle size distribution, lower porosity of the particles and allowing for a reduced quantity of alumoxane, which is acting as the binder.

Continuity Additives

In the polymerization processes disclosed herein, it may be desired to use a continuity additive, for example, to control or potentially even eliminate reactor discontinuity events, which in general are a disruption in the continuous operation of a polymerization reactor. As used herein, the terms "continuity additive," "continuity aid," and "antifoulant agent" refer to compounds or mixtures of compounds, such as solids or liquids, that are useful in gas phase or slurry phase polymerization processes to reduce or eliminate fouling of the reactor, where "fouling" may be manifested by any number of phenomena including sheeting of the reactor walls, plugging of inlet and outlet lines, formation of large agglomerates, or other forms of reactor upsets known in the art. For purposes here, the terms may be used interchangeably. In accordance with embodiments, the continuity additive may be used as a part of the catalyst composition or introduced directly into the reactor independently of the catalyst composition. In a class of embodiments, the continuity additive is supported on the inorganic oxide of the supported catalyst composition described herein.

The specific continuity additive used may depend at least in part upon the nature of the static charge, the particular polymer being produced, and/or the particular catalyst being used. Non-limiting examples of continuity additives comprise fatty acid amines, amide-hydrocarbon or ethoxylated-amide compounds such as described as "surface modifiers" in WO 96/11961; carboxylate compounds such as aryl-carboxylates and long chain hydrocarbon carboxylates, and fatty acid-metal complexes; alcohols, ethers, sulfate compounds, metal oxides and other compounds known in the art. Some specific examples of continuity additives include 1,2-diether organic compounds, magnesium oxide, ARMOSTAT 310, ATMER 163, ATMER AS-990, and other glycerol esters, IRGASTAT AS-990 and other ethoxylated amines (e.g., N,N-bis(2-hydroxyethyl)octadecylamine), alkyl sulfonates, and alkoxylated fatty acid esters; STADIS 450 and 425, KEROSTAT CE 4009 and KEROSTAT CE 5009, chromium N-oleylanthranilate salts, calcium salts of a Medialan acid and di-tert-butylphenol; POLYFLO 130, TOLAD 511 (a-olefin-acrylonitrile copolymer and polymeric polyamine), EDENOL D32, aluminum stearate, aluminum distearate, sorbitan-monooleate, glycerol monostearate, methyl toluate, dimethyl maleate, dimethyl furnarate, triethylamine, 3,3-diphenyl-3-(imidazol-1-yl)-propin, and like compounds. In some embodiments, the continuity additive is a metal carboxylate salt as described, optionally, with other compounds as described in this section.

Still other continuity additives can comprise polyethylenimines having the structure $-(CH_2-CH_2-NH)_n-$, where n can be from 10 to 10,000. The polyethyleneimines may be linear, branched, or hyperbranched (i.e., forming dendritic or arborescent polymer structures). They can be a homopolymer or copolymer of ethyleneimine or mixtures thereof (referred to as polyethyleneimine(s) hereafter). Although linear polymers represented by the chemical formula $-[CH_2 CH_2 NH]-$ may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Yet additional continuity additives can comprise a polyetheramine. As used herein, the term "polyetheramine" refers to a polymer containing a polyether backbone that terminates in at least one amino group. The polyether backbone may be, for example, ethylene oxide-based, propylene oxide-based, 1,2 butylene oxide-based, tetramethylene oxide-based, or any combination thereof. The polyetheramines may be, for example, a block copolymer, a graft copolymer, or a block-graft copolymer. In an embodiment, the polyetheramine is a diblock copolymer or a triblock copolymer. In an embodiment, the polyetheramine may be a block copolymer of ethylene oxide and propylene oxide. Suitable polyetheramines comprise, for example, monoamines, diamines, and triamines In an embodiment, the polyether backbone terminates in at least one primary amino group. In another embodiment, the polyether backbone terminates in at least one secondary amino group. In yet another embodiment, the polyether backbone terminates in at least one tertiary amino group. Suitable polyetheramines include those commercially available from Huntsman Corporation under the trade name JEFFAMINE® polyetheramines Examples of commercially available polyetheramines for use in embodiments of the present invention include, but are not limited to: JEFFAMINE® ED series polyetheramines, such as JEFFAMINE® HK-511 polyetheramine, JEFFAMINE® ED-600 polyetheramine, JEFFAMINE® ED-900 polyetheramine, and JEFFAMINE® ED-2003 polyetheramine; JEFFAMINE® M series polyetheramines, such as JEFFAMINE® M-600 polyetheramine, JEFFAMINE® M-1000, JEFFAMINE® M-2005 polyetheramine, and JEFFAMINE® M-2070 polyetheramine; and JEFFAMINE® D series polyetheramines, such as JEFFAMINE® D-230 polyetheramine, JEFFAMINE® D-400, JEFFAMINE® D-2000 polyetheramine, and JEFFAMINE® D-4000 polyetheramine Any of the aforementioned continuity additives may be employed either alone or in combination as a continuity additive. For example, the metal carboxylate salt may be combined with an amine containing control agent (e.g., an extracted carboxylate metal salt with any family member belonging to the KEMAMINE (available from Crompton Corporation) or ATMER (available from ICI Americas Inc.) family of products).

Other continuity additives useful in embodiments disclosed herein are well known to those in the art. Regardless of which continuity additives are used, care should be exercised in selecting an appropriate continuity additive to avoid introduction of poisons into the reactor. In addition, in selected embodiments, the smallest amount of the continuity additives necessary to bring the static charge into alignment with the desired range should be used.

The continuity additive can be introduced to the reactor as a combination of two or more of the above listed continuity additives. The continuity additive(s) can be introduced to the reactor in the form of a solution or slurry. The continuity additive can be introduced to the reactor as an individual feed or can be combined with other feeds prior to introduction to the reactor. For example, the continuity additive can be combined with the catalyst or catalyst slurry prior to introducing the combined catalyst slurry/continuity additive mixture to the reactor.

The continuity additive can be introduced to the reactor separate from the catalyst slurry. In other words, the continuity additive and the catalyst slurry can be contacted within the reactor. In additional examples, the continuity additive can be mixed with the catalyst slurry and then introduced to the reactor as a mixture. In other words, the continuity additive and the catalyst slurry can be contacted outside the reactor. In still another example, a first portion of the continuity additive can be mixed with the catalyst slurry and introduced to the reactor and a second portion of the continuity additive can be introduced separately to the reactor. In other words, a first portion of the continuity additive and the catalyst slurry can be contacted outside the reactor and a second portion of the continuity additive can be contacted within the reactor with the mixture of the catalyst slurry and first portion of the continuity additive.

The amount of continuity additive introduced to the reactor and/or the catalyst slurry can be sufficient to provide a continuity additive concentration of from about 0.05 ppmw to about 200 ppmw, based on the polymer production rate. For example, the continuity additive can be introduced to the reactor, i.e. directly to the reactor and/or combined with the catalyst slurry, in an amount ranging from a low of about 1 ppmw, about 2 ppmw, or about 3 ppmw to a high of about 35 ppmw, about 45 ppmw, or about 55 ppmw, based on the polymer production rate. The amount of continuity additive introduced to the reactor can depend, at least in part, on the particular catalyst composition, reactor pre-conditioning such as coatings to control static buildup, and/or other factors.

Polymerization Processes

Embodiments for producing polyolefins disclosed herein may employ any suitable process for the polymerization of olefins, including any suspension, solution, slurry, or gas phase process, using known equipment and reaction conditions, and are not limited to any specific type of polymerization system.

In general, the polymerization process may be a continuous gas phase process, such as a fluid bed process. In an embodiment, a fluid bed reactor may have a reaction zone and a velocity reduction zone (i.e., disengagement zone). The reaction zone includes a bed of growing polymer particles, formed polymer particles and a minor amount of catalyst particles fluidized by the continuous flow of the gaseous monomer and diluent to remove heat of polymerization through the reaction zone. Optionally, some of the recirculated gases may be cooled and compressed to form liquids that increase the heat removal capacity of the circulating gas stream when readmitted to the reaction zone. A suitable rate of gas flow may be readily determined by simple experiment. Makeup of gaseous monomer to the circulating gas stream is at a rate equal to the rate at which particulate polymer product and monomer associated therewith is withdrawn from the reactor, and the composition of the gas passing through the reactor is adjusted to maintain an essentially steady state gaseous composition within the reaction zone. The gas leaving the reaction zone is passed to the velocity reduction zone where entrained particles are removed. Finer entrained particles and dust may be removed in a cyclone and/or fine filter. The gas is passed through a heat exchanger wherein the heat of polymerization is removed, compressed in a compressor and then returned to the reaction zone.

Useful gas phase polymerization processes include those that utilize a fluidized bed reactor. This type reactor, and means for operating the reactor, are well known and are described in, for example, U.S. Pat. Nos. 3,709,853; 4,003,712; 4,011,382; 4,302,566; 4,543,399; 4,882,400; 5,352,749; 5,541,270; EP-A-0 802 202. These patents disclose gas phase polymerization processes wherein the polymerization medium is either mechanically agitated or fluidized by the continuous flow of the gaseous monomer and diluent.

The process described herein is suitable for the production of homopolymers of olefins, including ethylene, and/or copolymers, terpolymers, and the like, of olefins, including polymers comprising ethylene and at least one or more other olefins. The olefins may be alpha-olefins. The olefins, for example, may contain from 2 to 16 carbon atoms in one embodiment. In other embodiments, ethylene and a comonomer comprising from 3 to 12 carbon atoms, or from 4 to 10 carbon atoms, or from 4 to 8 carbon atoms, may be used. In an embodiment, the olefin is a monomer selected from the group consisting of ethylene, propylene, and any combination thereof.

In embodiments, polyethylene may be prepared by the process disclosed herein. Such polyethylene may include homopolymers of ethylene and interpolymers of ethylene and at least one alpha-olefin wherein the ethylene content is at least about 50% by weight of the total monomers involved. Olefins that may be used herein include ethylene, propylene, 1-butene, 1-pentene, 1-hexene, 1-heptene, 1-octene, 4-methylpent-l-ene, 1-decene, 1-dodecene, 1-hexadecene and the like. Also usable are polyenes such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene, and olefins formed in situ in the polymerization medium. When olefins are formed in situ in the polymerization medium, the formation of polyolefins containing long chain branching may occur.

The content of the alpha-olefin incorporated into the copolymer may be no greater than 30 mol % in total, or may be from 3 to 20 mol %. The term "polyethylene" when used herein is used generically to refer to any or all of the polymers comprising ethylene described above.

In other embodiments, propylene-based polymers may be prepared by processes disclosed herein. Such propylene-based polymers may include homopolymers of propylene and interpolymers of propylene and at least one alpha-olefin wherein the propylene content is at least about 50% by weight of the total monomers involved. Comonomers that may be used may include ethylene, 1-butene, 1-pentene, 1-hexene, 1-heptene, 1-octene, 4-methylpentene-1, 1-decene, 1-dodecene, 1-hexadecene and the like. Also usable are polyenes such as 1,3-hexadiene, 1,4-hexadiene, cyclopentadiene, dicyclopentadiene, 4-vinylcyclohexene-1, 1,5-cyclooctadiene, 5-vinylidene-2-norbornene and 5-vinyl-2-norbornene, and olefins formed in situ in the polymerization medium. When olefins are formed in situ in the polymerization medium, the formation of polyolefins containing long chain branching may occur. In one embodiment, the content of the alpha-olefin comonomer incorporated into a propylene-based polymer may be no greater than 49 mol % in total, from 3 to 35 mol % in other embodiments.

Hydrogen gas is often used in olefin polymerization to control the final properties of the polyolefin. Increasing the concentration (partial pressure) of hydrogen may increase the melt flow index (MFI) and/or melt index (MI) of the polyolefin generated. The MFI or MI can thus be influenced by the hydrogen concentration. The amount of hydrogen in the polymerization may be expressed as a mole ratio relative to the total polymerizable monomer, for example, ethylene, or a blend of ethylene and hexene or propylene. In an embodiment, the amount of hydrogen used in the polymerization processes is an amount sufficient to achieve the desired MFI or MI of the final polyolefin resin. Melt flow rate for polypropylene may be measured according to ASTM D 1238 (230° C. with 2.16 kg weight); melt index (I2) for polyethylene may be measured according to ASTM D 1238 (190° C. with 2.16 kg weight).

Other gas phase processes contemplated include series or multistage polymerization processes. For example, a staged reactor employing two or more reactors in series may be used, wherein one reactor may produce, for example, a high molecular weight component and another reactor may produce a low molecular weight component. In some embodiments, the polyolefin is produced using a staged gas phase reactor. Such polymerization systems are described in, for example, U.S. Pat. Nos. 5,627,242; 5,665,818; and 5,677,375; and European publications EP-A-0 794 200; EP-B1-0 649 992, EP-A-0 802 202 and EP-B-634 421.

In one embodiment, the one or more reactors in a gas phase or fluidized bed polymerization process may have a pressure ranging from about 0.7 to about 70 bar (about 10 to about 1,000 psia), or from about 14 to about 42 bar (about 200 to about 600 psia). In one embodiment, the one or more reactors may have a temperature ranging from about 10° C. to about 150° C., or from about 40° C. to about 125° C. In an embodiment, the reactor temperature may be operated at the highest feasible temperature taking into account the sintering temperature of the polymer within the reactor. In embodiments, the superficial gas velocity in the one or more reactors may range from about 0.2 to about 1.1 meters/second (about 0.7 to about 3.5 feet/second), or from about 0.3 to about 0.8 meters/second (about 1.0 to about 2.7 feet/second).

Some embodiments may be used with gas phase polymerization systems, at superatmospheric pressures in the range from 0.07 to 68.9 bar (1 to 1,000 psig), from 3.45 to 27.6 bar (50 to 400 psig) in some embodiments, from 6.89 to 24.1 bar (100 to 350 psig) in other embodiments, and temperatures in the range from 30 to 130° C., or from 65 to 110° C., from 75 to 120° C. in other embodiments, or from 80 to 120° C. in further embodiments. In some embodiments, operating temperatures may be less than 112° C. In embodiments, stirred or fluidized bed gas phase polymerization systems may be used.

The polymerization process may be a continuous gas phase process that includes the steps of: (a) introducing a recycle stream (including ethylene and alpha olefin monomers) into the reactor; (b) introducing the supported catalyst composition; (c) withdrawing the recycle stream from the reactor; (d) cooling the recycle stream; (e) introducing into the reactor additional monomer(s) to replace the monomer(s) polymerized; (f) reintroducing the recycle stream or a portion thereof into the reactor; and (g) withdrawing a polymer product from the reactor.

In embodiments, one or more olefins, $C_2$ to $C_{30}$ olefins or alpha-olefins, including ethylene or propylene or combinations thereof, may be prepolymerized in the presence of a metallocene catalyst composition prior to the main polymerization. The prepolymerization may be carried out batchwise or continuously in gas, solution or slurry phase, including at elevated pressures. The prepolymerization may take place with any olefin monomer or combination and/or in the presence of any molecular weight controlling agent such as hydrogen. For examples of prepolymerization procedures, see U.S. Pat. Nos. 4,748,221; 4,789,359; 4,923,833; 4,921,825; 5,283,278; and 5,705,578 and European publication EP-B-0279 863 and WO 97/44371.

Processes disclosed herein may optionally use inert particulate materials as fluidization aids. These inert particulate materials can include carbon black, silica, talc, and clays, as well as inert polymeric materials. Carbon black, for example, has a primary particle size of about 10 to about 100 nanometers, an average size of aggregate of about 0.1 to about 30 microns, and a specific surface area from about 30 to about 1500 $m^2/g$. Silica has a primary particle size of about 5 to about 50 nanometers, an average size of aggregate of about 0.1 to about 30 microns, and a specific surface area from about 50 to about 500 $m^2/g$. Clay, talc, and polymeric materials have an average particle size of about 0.01 to about 10 microns and a specific surface area of about 3 to 30 $m^2/g$. These inert particulate materials may be used in amounts ranging from about 0.3 to about 80%, or from about 5 to about 50%, based on the weight of the final product. They are especially useful for the polymerization of sticky polymers as disclosed in U.S. Pat. Nos. 4,994,534 and 5,304,588.

Chain transfer agents, promoters, scavenging agents and other additives may be, and often are, used in the polymerization processes disclosed herein. Chain transfer agents are often used to control polymer molecular weight. Examples of these compounds are hydrogen and metal alkyls of the general formula $M^xR_y$, where M is a Group 3-12 metal, x is the oxidation state of the metal, typically 1, 2, 3, 4, 5 or 6, each R is independently an alkyl or aryl, and y is 0, 1, 2, 3, 4, 5, or 6. In some embodiments, a zinc alkyl is used, such as diethyl zinc. Typical promoters may include halogenated hydrocarbons such as $CHCl_3$, $CFCl_3$, $CH_3-CCl_3$, $CF_2Cl-CCl_3$, and ethyltrichloroacetate. Such promoters are described in, for example, U.S. Pat. No. 4,988,783. Other organometallic compounds such as scavenging agents for poisons may also be used to increase catalyst activity. Examples of these compounds include metal alkyls, such as aluminum alkyls, for example, triisobutylaluminum. Some compounds may be used to neutralize static in the fluidized-bed reactor, others known as drivers rather than antistatic agents, may consistently force the static from positive to negative or from negative to positive. The use of these additives is well within the skill of those skilled in the art.

These additives may be added to the circulation loops, riser, and/or downer separately or independently from the catalyst, or as part of the catalyst In embodiments, the reactors disclosed herein are capable of producing greater than 500 lbs of polymer per hour (227 kg/hr) to about 300,000 lbs/hr (136,000 kg/hr) or higher of polymer, preferably greater than 1000 lbs/hr (455 kg/hr), more preferably greater than 10,000 lbs/hr (4540 kg/hr), even more preferably greater than 25,000 lbs/hr (11,300 kg/hr), still more preferably greater than 35,000 lbs/hr (15,900 kg/hr), still even more preferably greater than 50,000 lbs/hr (22,700 kg/hr) and most preferably greater than 65,000 lbs/hr (29,000 kg/hr) to greater than 150,000 lbs/hr (68,100 kg/hr).

The polymers produced by embodiments of the process of the invention can be used in a wide variety of products and end-use applications. The polymers produced by the process of the invention may include, but are not limited to, linear low density polyethylene, low density polyethylenes, and high density polyethylenes.

The polymers, including ethylene and propylene based polymers, have a density, for example, in the range of from about 0.86 g/cm$^3$ to about 0.97 g/cm$^3$. In other embodiments, the polymers have a density in the range of from about 0.88 g/cm$^3$ to about 0.965 g/cm$^3$ or in the range of from about 0.900 g/cm$^3$ to about 0.96 g/cm$^3$. Density is measured according to ASTM D-792.

The polymers produced by the process of the invention may have a molecular weight distribution, a weight average molecular weight to number average molecular weight (Mw/Mn), for example, of greater than 1.5 to about 15. In other embodiments, the polymers may have an Mw/Mn of greater than 2 to about 10 or greater than about 2.2 to less than about 8. Mw, Mn, and z-average molecular weight (Mz) can be measured using gel permeation chromatography (GPC), also known as size exclusion chromatography (SEC). This technique utilizes an instrument containing columns packed with porous beads, an elution solvent, and detector in order to separate polymer molecules of different sizes. Measurement of molecular weight by SEC is well known in the art and is discussed in more detail in, for example, Slade, P. E. Ed., Polymer Molecular Weights Part II, Marcel Dekker, Inc., NY, (1975) 287-368; Rodriguez, F., Principles of Polymer Systems 3rd ed., Hemisphere Pub. Corp., NY, (1989) 155-160; U.S. Pat. No. 4,540,753; and Verstrate et al., *Macromolecules*, vol. 21, (1988) 3360; T. Sun et al., Macromolecules, vol. 34, (2001) 6812-6820.

The polymers of the present invention may have a melt index (MI) or ($I_2$) as measured by ASTM-D-1238-E (190° C./2.16 kg), for example, in the range from 0.01 dg/min to 1000 dg/min. In other embodiments, the polymers may have a melt index of from about 0.01 dg/min to about 100 dg/min or from about 0.1 dg/min to about 100 dg/min.

The polymers of the invention in an embodiment may have a melt index ratio ($I_{21}/I_2$) ($I_{21}$ is measured by ASTM-D-1238-F, [190° C./21.6 kg]), for example, of from 5 to 300. In other embodiments, the polymers may have a melt index ration of from about 10 to less than 250, from 15 to 200, or from 20 to 180.

The polymers of the invention may be blended and/or coextruded with any other polymer. Non-limiting examples of other polymers include linear low density polyethylenes produced via conventional and/or single-site catalysis, elastomers, plastomers, high pressure low density polyethylene, high density polyethylenes, polypropylenes and the like.

Polymers produced by the process of the invention and blends thereof are useful in such forming operations as film, pipe, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers may include, are not limited to, melt spinning, solution spinning and melt blown fiber operations for use in woven or nonwoven form to make filters, diaper fabrics, medical garments, geotextiles, etc. Extruded articles may include medical tubing, wire and cable coatings, geomembranes, and pond liners. Molded articles include single and multi-layered constructions in the form of bottles, tanks, large hollow articles, rigid food containers and toys, etc.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used. In the preceding description and the appended claims, the singular forms "a," "an" and "the" include plural referents unless otherwise specified.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited; in the same way, ranges from any upper limit may be combined with any other upper limit to recite a range not explicitly recited.

All documents and references cited herein, including testing procedures, publications, patents, journal articles, etc. are herein fully incorporated by reference for all jurisdictions in which such incorporation is permitted and to the extent such disclosure is consistent with the description of the present invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Although individual embodiments are discussed, the invention covers all combinations of all those embodiments.

What is claimed is:

1. A method for integrating aluminoxane production into catalyst production, comprising:
   reacting a hydrocarbyl aluminum compound and water in a recycled solvent to produce at least a reaction mixture comprising an aluminoxane, a remainder of the hydrocarbyl aluminum compound, and the recycled solvent;

combining at least a portion of the reaction mixture with a catalyst component to produce at least a catalyst composition;

separating the catalyst composition from the recycled solvent in the reaction mixture; and recycling at least a portion of the separated solvent for producing additional aluminoxane, the separated solvent comprising at least a portion of the remainder of the hydrocarbyl aluminum compound.

2. The method of claim 1, wherein reacting the hydrocarbyl aluminum compound and the water comprises circulating the hydrocarbyl aluminum compound and the water in a reactor loop.

3. The method of claim 1, further comprising withdrawing the reaction mixture from the reactor loop.

4. The method of claim 1, wherein the combining at least a portion of the reaction mixture comprises introducing a catalyst component into the reactor loop.

5. The method of claim 4, wherein the catalyst component is introduced into a degassing vessel for removing gas from the reaction mixture.

6. The method of claim 1, wherein the combining at least a portion of the reaction mixture comprises introducing a support material into the reactor loop such that the reaction mixture further comprises the support material.

7. The method of claim 1, further comprising combining a support material with the recycled solvent prior to the step of reacting the hydrocarbyl aluminum compound and the water.

8. The method of claim 1, wherein the aluminoxane produced in the step of reacting a hydrocarbyl aluminum compound and the water is not concentrated prior to the step of combining at least a portion of the reaction mixture with the catalyst component.

9. The method claim 1, further comprising drying the catalyst composition to produce a dried catalyst composition and a gaseous stream comprising the solvent.

10. The method of claim 9, wherein the step of drying comprises spray drying the catalyst composition.

11. The method of claim 1, wherein the method is a continuous flow process.

12. The method of claim 1, wherein the aluminoxane comprises an oligomeric compound comprising Al(R)—O subunits, wherein R is a $C_1$ to $C_8$ alkyl group.

13. The method of claim 1, wherein the aluminoxane comprises methylaluminoxane.

14. The method of claim 1, wherein the catalyst component comprises at least one catalyst selected from the group consisting of a metallocene catalyst, a Ziegler-Natta catalyst, a Phillips-type chromium catalyst, a Group 15-containing catalyst, an $AlCl_3$, catalyst, a cobalt catalyst, an iron catalyst, a palladium catalyst, and any combination thereof.

15. A method for integrating aluminoxane production into catalyst production, comprising:

circulating a fluid in a reactor loop, the fluid comprising a recycled solvent and a first quantity of a hydrocarbyl aluminum compound;

introducing water and a second quantity of a hydrocarbyl aluminum compound into the reactor loop;

allowing the water and the hydrocarbyl aluminum compound to react in the recycled solvent to produce at least a reaction mixture comprising an aluminoxane, a remainder of the hydrocarbyl aluminum compound, and the recycled solvent;

introducing a catalyst component into the reactor loop to produce at least a catalyst composition;

separating the catalyst composition from the recycled solvent; and recycling at least a portion of the separated solvent for producing additional aluminoxane, the separated solvent comprising at least a portion of the remainder of the hydrocarbyl aluminum compound.

16. The method of claim 15, wherein the catalyst component is introduced into the reactor loop after the introducing water and a second quantity of a hydrocarbyl aluminum compound has ceased.

17. The method of claim 15, further comprising introducing a silica support material into the reactor loop.

18. The method of claim 17, wherein the silica support is introduced into the reactor loop prior to the introducing water and a second quantity of a hydrocarbyl aluminum compound.

19. A method for integrating aluminoxane production into catalyst production, comprising:

reacting a hydrocarbyl aluminum compound and an oxygen source in a recycled solvent to produce at least a reaction mixture comprising an aluminoxane, a remainder of the hydrocarbyl aluminum compound, and the recycled solvent;

combining at least a portion of the reaction mixture with a catalyst component to produce at least a catalyst composition;

separating the catalyst composition from the recycled solvent in the reaction mixture; and recycling at least a portion of the separated solvent for producing additional aluminoxane, the separated solvent comprising at least a portion of the remainder of the hydrocarbyl aluminum compound.

* * * * *